United States Patent [19]
Bade

[11] Patent Number: 4,630,469
[45] Date of Patent: Dec. 23, 1986

[54] SAMPLE HOMOGENIZER
[75] Inventor: Robert K. Bade, Bartlesville, Okla.
[73] Assignee: Phillips Petroleum Company, Bartlesville, Okla.
[21] Appl. No.: 781,563
[22] Filed: Sep. 30, 1985
[51] Int. Cl.⁴ .......................................... G01N 30/02
[52] U.S. Cl. ................................ 73/61.1 C; 210/659; 210/198.2
[58] Field of Search .................. 73/864.81, 61.1 C; 210/635, 656, 198.2, 659; 436/161; 422/70

[56] References Cited
U.S. PATENT DOCUMENTS

| 4,007,636 | 2/1977 | Wahl | 73/290 R |
| 4,116,046 | 9/1978 | Stein | 73/61.1 C |
| 4,204,952 | 5/1980 | Snyder | 210/659 |
| 4,274,967 | 6/1981 | Snyder | 210/198.2 |
| 4,419,452 | 12/1983 | Imai et al. | 436/161 |
| 4,454,043 | 6/1984 | Ting et al. | 210/659 |

Primary Examiner—Stewart J. Levy
Assistant Examiner—Robert R. Raevis
Attorney, Agent, or Firm—A. W. Umphlett

[57] ABSTRACT

A chromatograph sample homogenizer having a mixing chamber containing means for homogenizing a mixture therein and means of controlled ingress and/or controlled egress for (1) eluant from a chromatographic column, (2) wash solvent, (3) transport gas, (4) waste material, and (5) homogenized sample. Methods for manipulating the operation of the sample homogenizer to provide homogenized samples and homogenized diluted samples.

7 Claims, 1 Drawing Figure

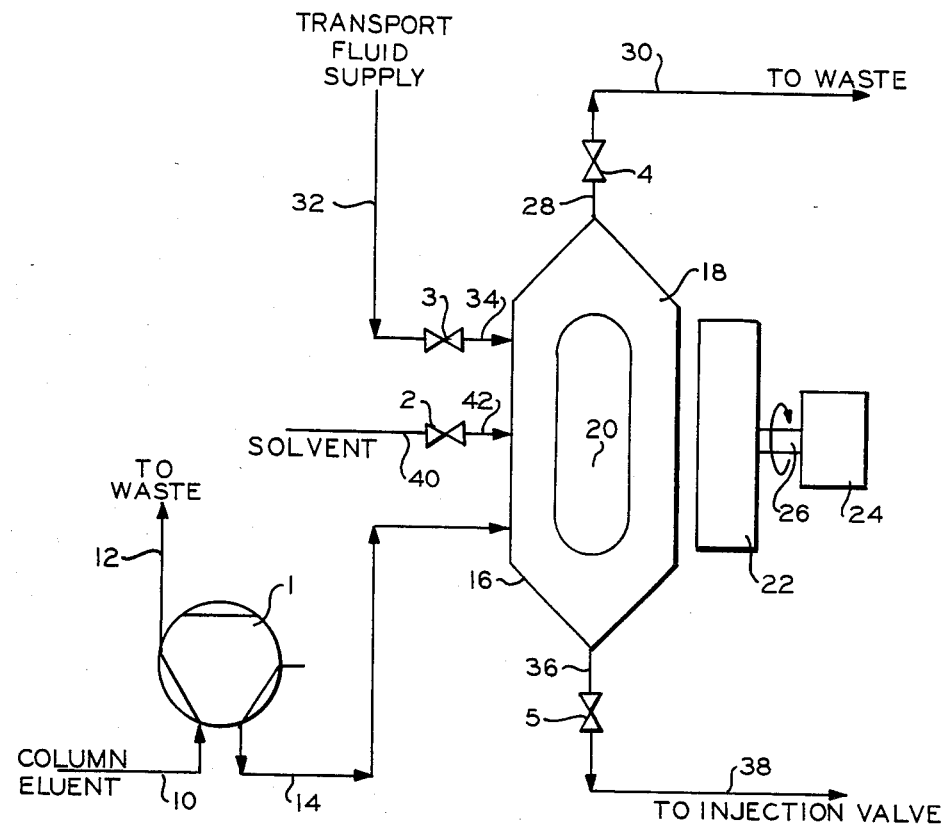

SAMPLE HOMOGENIZER

BACKGROUND OF THE INVENTION

This invention relates to sample homogenization. In one of its aspects this invention relates to the handling of chromatographic samples. In another of its aspects this invention relates to liquid chromatography in which there are components that have widely different peak sizes. In another aspect of this invention it relates to gas chromatography in which the samples contain polymers or other non-volatile materials.

When liquid process stream samples having a wide range of constituent concentrations beyond the dynamic range of the detector system are analyzed by chromatographic means a problem can develop in accurately measuring both the large peaks and the small peaks. Dilution oi a sample sufficiently to allow the large peaks to be measured can cause an inadequate signal for the small peaks. The present invention describes an apparatus and method for its use which will allow the capture of the large peaks for reinjection into either a liquid chromatograph or a gas chromatograph.

Similarly, in the gas chromatographic analysis of process gas stream samples having entrained polymeric or other non-volatile materials injection valves and/or columns of the analytical equipment tend to become clogged. These problems can be avoided by chromatographically separating the non-volatiles by liquid chromatography using size exclusion, partition or adsorption modes and collecting the volatile components in the device of the present invention for injection into an analysis by a gas chromatograph.

It is therefore an object of this invention to provide an apparatus for collecting and mixing eluant from a chromatograph to provide homogenized sample for a subsequent chromatographic analysis. It is another object of this invention to provide a method for operating a collection and mixing device so that eluant from a chromatographic separation can be collected and homogenized for analysis in a subsequent chromatographic operation.

Other aspects, objects and the various advantages of this invention will become apparent upon reading the specification, studying the drawing and reading the appended claims.

STATEMENT OF THE INVENTION

According to this invention, a chromatograph sample homogenizer is provided which is a mixing chamber containing means for homogenizing mixture therein and having connected to the mixing chamber several means of ingress or egress each of which has a valve and connecting conduit to provide (a) a first valved inlet for eluant and transport fluid from a chromatographic column, (b) a second valved inlet for solvent, (c) a third valved inlet for transport fluid supply, (d) a fourth valved outlet for waste, and (e) a fifth valved outlet for sample injection to a downstream analyzer.

In a preferred embodiment of this invention the mixing chamber containing means for homogenizing the mixture therein, is an enclosed chamber of sufficient size to contain a magnetic stirring bar with the stirring bar activated by an externally located means such as a rotating magnet or an oscillating magnetic field so that a similar motion can be induced in the stirring bar.

In an embodiment of the invention a method is provided, using the device described above, for providing homogenized sample in which: (a) the second, third and fifth valves are closed and the first and fourth valves are open until sample is passed through the homogenizer; (b) the fourth valve is closed thereby collecting sample in the homogenizer; (c) the first valve is closed; (d) the homogenizing means is activated for a time sufficient to mix the sample; and (e) third and fifth valves are open to pass sample from the homogenizer to a downstream analyzer.

In an embodiment of the invention a method is provided for handling a chromatographic sample in which the sample is separated by volatility or peak size, the eluant from this separating is passed into a chromatographic sample homogenizer as described above, the sample is homogenized, and the sample is then injected into a downstream analyzer.

In another embodiment of the invention a method is provided for diluting an analytical sample using the apparatus and method as described above, in which: (a) the second, third and fifth valves are closed and the first and fourth valves are open until sample is passed through the homogenizer; (b) the fourth valve is closed so that sample is collected in the homogenizer; (c) the first valve is closed; (d) optionally, homogenizing means is activated for a time sufficient to mix the sample; and (e) the third and fourth valves are opened for a time sufficient to purge sample from the homogenizing chamber and introduce a desired amount of transport fluid as dilution fluid partially thereby replacing sample with dilution fluid; (f) said third valve and said fourth valve are closed; (g) the homogenizing means is activated for a time sufficient to mix the sample; (h) the third and fifth valves are opened to pass sample from the homogenizer to a downstream analyzer.

In a further embodiment of the invention a method is provided for diluting an analytical sample using the apparatus and method as described above, in which: (a) the second, third and fifth valves are closed and the first and fourth valves are open until sample is passed through the homogenizer; (b) the fourth valve is closed so that sample is collected in the homogenizer; (c) the first valve is closed; (d) optionally, homogenizing means is activated for a time sufficient to mix the sample; and (e) the second and fourth valves are opened for a time sufficient to purge sample from the homogenizing chamber and introduce a desired amount of solvent as dilution fluid partially thereby replacing sample with dilution fluid; (f) the second valve and the fourth valve are closed; (g) the homogenizing means is activated for a time sufficient to mix the sample; (h) the third and fifth valves are opened to pass sample from the homogenizer to a downstream analyzer. It is also within the scope of the invention to use the transport fluid from the column as a dilution fluid. To accomplish this, substitute steps (e) and (f) as follows for the like-identified steps in the dilution process set out immediately above so that: (e) the first and fourth valves are opened for a time sufficient to introduce a desired amount of transport fluid as dilution fluid and (f) subsequently both valves are closed with steps (g) and (h) following as set out above.

In a still further embodiment of the invention a method is provided in which, after the homogenized sample has been injected into a downstream analyzer the chromatographic sample homogenizer is rinsed with sufficient solvent or transport fluid to remove the sample and prepare the homogenizer for entry of a subsequent sample.

The invention can best be understood in conjunction with the drawing which is a schematic representation of the apparatus useful in the present invention.

Referring now to the drawing eluant and transport fluid from a chromatograph is passed through line 10 and switching valve 1 to waste through line 12. Upon switching, valve 1 allows passage of the column eluant through line 14 into the sample homogenizer 16.

The sample homogenizer 16 is composed of a chamber 18 having therein a magnetic stirring bar 20 which is activated by a rotating magnet 22 when the magnet is rotated by motor 24 through connecting shaft 26.

The eluant is allowed to pass through chamber 18, line 28, valve 4, and waste line 30. Valves 2, 3, and 5 are in closed positions. Valve 4 is then closed allowing chamber 18 to be filled and pressurized with eluant. Switching valve 1 is then moved to closed position. Motor 24 is then activated turning shaft 26 and magnet 22 thereby causing the magnetic stirring bar 20 within chamber 18 to be rotated thereby homogenizing the sample within chamber 18.

After a suitable homogenization period valves 5 and 3 are opened so that a carrier or transport fluid can be admitted through line 32, valve 3, and line 34 into the chamber 18 to force the sample through line 36, valve 5, and line 38 to be injected into a downstream chromatograph (not shown). It is envisioned that the transport fluid can be either a liquid or a gas based upon the type of downstream analyzer.

If dilution of the sample is desirable, after closing switching valve 1 to contain eluant within the homogenization chamber as described above, motor 24 can be activated to provide the homogenizing action, as described above. Valves 3 and 4 are open for a time sufficient to pass the desired amount of sample from chamber 18 and to admit the desired amount of dilution fluid through line 34. In an alternative valve 1 could be opened in place of valve 3 to utilize carrier fluid to dilute the sample. Valves 3 and 4 are then closed and motor 24 is activated to provide the homogenizing action of magnetic stirring bar 20. After homogenization valves 3 and 5 can be opened to pass the homogenized sample to the analytical instrument. This sequence can be used when the downstream analyzer is a liquid chromatograph.

If dilution of the sample is desirable where the downstream analyzer is a gas chromatograph, after closing switching valve 1 to contain eluant within the homogenization chamber as described above, motor 24 can be activated to provide the homogenizing action, as described above. Valves 2 and 4 are open for a time sufficient to pass the desired amount of sample from chamber 18 and to admit the desired amount of solvent as dilution fluid through line 42. Alternatively valve 1 could be opened in place of valve 2 to utilize carrier fluid to dilute the sample. Valves 2 and 4 are then closed and motor 24 is activated to provide the homogenizing action of magnetic stirring bar 20. After homogenization valves 3 and 5 can be opened to pass the homogenized sample to the analytical instrument. In this situation the transport fluid can be a gas such as Helium and cannot be used to dilute the sample.

After the sample has been transferred valves 3 and 5 are closed and valves 2 and 4 are opened so that solvent can be transferred through line 40, valve 2 and line 42, through the chamber 18 and line 28, valve 4 and line 30 to be discarded as waste. Carrier or transport fluids through valves 1 and 3 respectfully can be utilized as a wash fluid for the homogenizer. Valves 2 and 4 are then closed. If desired, the agitation mechanism can be activated. Valves 3 and 5 are then opened to flush the solvent from the chamber and through line 36, valve 5 and line 38 for discarding at the subsequent chromatograph. The washing-flushing with gas process is repeated as necessary to remove the sample from the system. All of the valves in the system are then closed so that the system is shut in awaiting another sample.

The normal sequence for activation of valves in the system is to open valves 1 and 4 to purge column eluant through the clean system; close valves 1 and 4 and activate the agitation system; shut down the agitation system and open valves 3 and 5 to transfer the sample into the subsequent chromatograph system; close valves 3 and 5 and open valves 2 and 4 to provide wash solvent through the chamber; agitate the wash solvent if desired; then close valves 2 and 4 and open valves 3 and 5 to purge the wash solvent from the chamber and through the injection line to the subsequent chromatograph. The filling with wash solvent and purging from the system to the subsequent chromatograph system is repeated as necessary.

The system as described above is well suited for automatic operation so that it is within the ambit of this invention to provide a timed controlled system for operating the valves in sequence.

The following are examples of the operation of this invention which should be taken as illustrative and not restrictive.

EXAMPLE I

The invention was used as a homogenizer in the analysis of butadiene/styrene co-polymers. The original mixture containing high molecular weight polymer and low molecular weight monomers was directed to a liquid chromatograph (LC) using tetrahydrofuran (THF) as the carrier fluid in order to separate the high molecular weight polymer from the low molecular weight monomers. The low molecular weight monomer mixture was directed to the homogenizer for subsequent analysis in a gas chromatograph.

The prototype homogenization chamber for this invention was constructed of a cylindrical glass central body approximately 2½ inches long and having an internal diameter of about ¾ inch resulting in approximately a 5 ml volume. Stainless steel caps containing Teflon sealing O-rings were clamped in position to enclose the central body with the stainless steel caps being fitted with 1/16 inch OD, stainless steel tubing to provide inlet and outlet ports. The stirring bar was an elongated teflon coated flattened metallic bar that occupied approximately 30 percent of the volume of the chamber. The inlet ports for gas supply and wash solvent and the outlet ports to waste and the analytical equipment were fitted with air actuated 2-way Skinner solenoid valves available from Applied Automation, Bartlesville, Okla. The eluent inlet line also 1/16 inch ID was fitted with a six port pneumatic operated model 20 valve from Applied Automation, Bartlesville, Okla. The means for operating the stirring bar was a 2000–3600 rpm ring magnet externally mounted clock motor with the homogenizer positioned within the magnetic ring.

The polymer fractions eluted from the LC column at rates of 1 to 1½ cc/min and were initially directed to waste. At the time of elution of the polystyrene monomer in solution with the THF, valve 1 was switched to direct the sample to the homogenizer. After two minutes (about 3-4 ml volume) valve 1 and valve 4 were switched closed so that the homogenizer contained about 4 ml of liquid and 1 ml of air (headspace). After two minutes of stirring using the magnetic stirring motor, valves 3 and 5 were opened and the homogenized sample was directed to a subsequent gas chromatograph using a helium carrier gas.

Though not performed in this analysis cycle the homogenizer is designed to be washed as described above using THF solvent as washing solution. The invention was successfully used as a homogenizer and coupling interface between differing phase analytical apparatus.

EXAMPLE II

A solution of
40% Acrylonitrile
50% Styrene
4% Ethylbenzene
4% Methylethylketone (MEK)
2% Terpinolene
was diluted at a 2800/1 ratio with acetonitrile connected via the transport line for analysis in a liquid chromatograph capable of examining all components except the MEK. A two µl sample of the above solution was retained in the homogenizer by injecting the acetonitrile via a model 20 AAI valve into the 5 ml liquid volume apparatus described in Example I. This was accomplished by opening valves 3 and 4 during the injection. After closing valves 3 and 4 the diluted solution was blended for two minutes resulting in a 0.036% homogenized mixture concentration as compared to the original sample. Valve 3 and 5 were then opened and, utilizing helium pressure, the diluted sample was directed to a liquid chromatograph.

I claim:
1. A chromatograph sample homogenizer comprising a mixing chamber containing means for homogenizing a mixture therein and connected thereto:
   (a) a first valved inlet for eluant from a chromatographic column comprising a first valve and connecting conduit;
   (b) a second valved inlet for solvent comprising a second valve and connecting conduit;
   (c) a third valved inlet for transport fluid supply comprising a third valve and connecting conduit;
   (d) a fourth valved outlet for waste comprising a fourth valve and connecting conduits; and
   (e) a fifth valved outlet for sample injection to a downstream analyzer comprising a fifth valve and connecting conduit.
2. A method for handling a chromatographic sample using an apparatus comprising a mixing chamber containing means for homogenizing a mixture therein and connected thereto:
   (1) a first valved inlet for eluant from a chromatographic column comprising a first valve and connecting conduit;
   (2) a second valved inlet for solvent comprising a second valve and connecting conduit;
   (3) a third valved inlet for transport fluid supply comprising a third valve and connecting conduit;
   (4) a fourth valved outlet for waste comprising a fourth valve and connecting conduits; and
   (5) a fifth valved outlet for sample injection to a downstream analyzer comprising a fifth valve and connecting conduit said method comprising:
   (a) passing material to be sampled through said apparatus with said second, third and fifth valves closed and said first and fourth valves open;
   (b) closing said fourth valve thereby collecting material in said apparatus;
   (c) closing said first valve;
   (d) opening said third and fourth valves for a time sufficient partially to replace said material with transport fluid;
   (e) closing said third and fourth valves;
   (f) activating said homogenizer for a time sufficient to mix said transport fluid and said material;
   (g) opening said third and fifth valves to pass a mixture of said transport fluid and said material from said apparatus.
3. A method of claim 2 wherein said homogenizing means is activated between steps (c) and (d) for a time sufficient to homogenize said material.
4. A method for handling a chromatographic sample comprising:
   (a) separating a sample by volatility or peak size,
   (b) passing eluant from said separating into a chromatograph sample homogenizer comprising a mixing chamber containing means for homogenizing a mixture therein and connected thereto:
      (1) a first valved inlet for eluant from a chromatographic column comprising a first valve and connecting conduit;
      (2) a second valved inlet for solvent comprising a second valve and connecting conduit;
      (3) a third valved inlet for transport fluid supply comprising a third valve and connecting conduit;
      (4) a fourth valved outlet for waste comprising a fourth valve and connecting conduits; and
      (5) a fifth valved outlet for sample injection to a downstream analyzer comprising a fifth valve and connecting conduit said method comprising
   (c) homogenizing said sample, and
   (d) injecting said sample into a downstream analyzer.
5. A method of claim 4 wherein subsequent to said homogenizing of said sample said chromatographic sample homogenizer is rinsed with sufficient wash solvent to remove residue of said sample.
6. A method of claim 5 wherein rinsing said homogenizer with wash solvent is accomplished by:
   (e) closing said first, third and fifth valves;
   (f) opening said second and fourth valves;
   (g) closing said second and fourth valves;
   (h) opening said third and fifth valves; and
   (i) repeating step (e)-(h) sequentially until the system is purged of sample.
7. A method of claim 4 wherein passing eluant from said separating, homogenizing, and injecting sample into said downstream analyzer is accomplished by:
   (a) closing said second, third and fifth valves and opening said first and fourth valves until sample is passed through said homogenizer;
   (b) closing said fourth valve and collecting sample in said homogenizer;
   (c) activating homogenizer for a time sufficient to mix the sample; and
   (d) opening said third and fifth valves to pass sample from said homogenizer to the downstream analyzer.

* * * * *